United States Patent [19]
Grafen et al.

[11] 4,191,692
[45] Mar. 4, 1980

[54] MANUFACTURE OF TOCOPHEROL

[75] Inventors: Paul Grafen, Weisenheim; Henning Kroesche, Frankenthal; Bernhard Schulz, Schwetzingen; Joachim Paust, Neuhofen; Sigberg Pfohl, Speyer, all of Fed. Rep. of Germany

[73] Assignee: BASF Aktiengesellschaft, Fed. Rep. of Germany

[21] Appl. No.: 896,479

[22] Filed: Apr. 14, 1978

Related U.S. Application Data

[63] Continuation of Ser. No. 763,646, Jan. 28, 1977, abandoned.

[30] Foreign Application Priority Data

Feb. 20, 1976 [DE] Fed. Rep. of Germany ....... 2606830

[51] Int. Cl.$^2$ ............................................ C07D 311/72
[52] U.S. Cl. ................................................. 260/345.5
[58] Field of Search ........................... 260/345.5, 345.6

[56] References Cited

U.S. PATENT DOCUMENTS

| | | | |
|---|---|---|---|
| 3,444,213 | 5/1969 | Nelan | 260/345.5 |
| 3,708,505 | 1/1973 | Greenbaum et al. | 260/345.5 |

*Primary Examiner*—Nicky Chan
*Attorney, Agent, or Firm*—Keil & Witherspoon

[57] ABSTRACT

In the manufacture of tocopherol (vitamin E) by reaction of isophytol with trimethylhydroquinone in the presence of zinc chloride and acid in a hydrocarbon solvent one of the starting compounds, isophytol, is pretreated with small amounts of ammonia or an amine.

Tocopherol is obtained in higher yield and purity.

13 Claims, No Drawings

MANUFACTURE OF TOCOPHEROL

This is a continuation of application Ser. No. 763,646 filed Jan. 28, 1977, now abandoned.

The present invention relates to an improved process for the manufacture of tocopherol by condensing trimethylhydroquinone with isophytol or phytol by means of zinc chloride and a proton donor such as hydrogen chloride, in which isophytol or phytol is treated with an amine or ammonia prior to the condensation.

The reaction of trimethylhydroquinone with isophytol in heptane as the solvent in the presence of zinc chloride or other Lewis acids and hydrochloric acid gas or other proton donors at 100° C. under atmospheric pressure, to give d,l-α-tocopherol (vitamin E) has been disclosed. It is true that this process can be carried out relatively simply, but both the yield and the purity of the end product required improvement.

Attempts have therefore already been made to carry out the reaction in accordance with German Laid-Open Application DOS No. 1,909,164, using a boron trifluoride complex or aluminum trichloride complex of trimethylhydroquinone at a lower temperature.

Iron powder, or iron-II chloride and hydrogen chloride, have also already been proposed, in German Laid-Open Application No. 2,160,103.

However, with these processes it was only possible to improve either the purity or the yield.

It is an object of the present invention to improve the yield of the condensation process which is industrially the simplest to carry out, ie. the process using zinc chloride and hydrogen chloride, and simultaneously to improve the purity of the end products.

We have found, surprisingly, that this object is achieved and that the reaction of 2,3,5-trimethylhydroquinone with isophytol or phytol in the presence of zinc chloride and proton donors takes place with better yield, and with the formation of less by-products, if the isophytol or phytol has been treated, prior to the reaction, with small amounts of ammonia or a primary or secondary aliphatic, cycloaliphatic or araliphatic amine at a normal or elevated temperature, especially at from 20° to 200° C.

As a rule, the treatment is carried out with amounts of amine exceeding 100 ppm, eg. with from 0.05 to 5, preferably from 0.1 to 2, percent by weight of ammonia or amine, based on isophytol or phytol. Even higher amounts of amine can also be used, but this does not result in any further advantage. If amounts greater than 0.5 percent by weight are used, it is advisable to remove the excess amine, before continuing the reaction, by distillation under atmospheric pressure or reduced pressure.

The treatment with the amine is advantageously carried out by mixing the latter with isophytol or phytol and heating the mixture, eg. at from 20° to 200° C., preferably from 50° to 120° C. The treatment may also be carried out at below 20° C., but this increases the duration of the treatment substantially, and it is advisable to use solvents, because of the viscosity of phytol or isophytol at low temperatures. For this reason, it is technically advantageous to carry out the process at a slightly elevated temperature. The treatment according to the invention can also be carried out at above 200° C., eg. at up to 220° C., if the heating is kept sufficiently brief to avoid decomposition of the phytol or isophytol. Accordingly, the limit imposed on the treatment temperature is essentially the temperature at which significant decomposition of phytol or isophytol commences. The amine may be added undiluted or as a solution in a solvent, eg. heptane.

Depending on the temperature chosen, the chosen duration of treatment may be from a few seconds to 100 hours. A duration of from one to 15 hours at from 50° to 100° C. is preferred if the treatment is carried out batchwise. It is also possible to heat the isophytol or phytol, mixed with the amine, to from 60° to 180° C., preferably from 90° to 130° C., in a heating zone with a residence time of from 30 minutes down to 0.3 minute, and to feed the hot isophytol or phytol directly to the reaction.

The treatment with ammonia is carried out in the same manner as that described for the amines, but the use of the amines is preferred, because they are more effective.

The isophytol, pretreated according to the invention with ammonia or an amine, which is employed as the starting material may also be a product obtained by catalytic hydrogenation of dehydroisophytol in the presence of an amine or ammonia.

Suitable amines are aliphatic, cycloaliphatic and araliphatic amines of 1 to 20 carbon atoms in the chain. Amongst these, the primary alkyl monoamines, which may have straight or branched chains, are preferred. Specific examples of suitable aliphatic amines are isopropylamine, n-butylamine, iso-butylamine, diethylamine and especially monomethylamine, stearylamine and tridecylamine (an isomer mixture obtained from tetrameric propylene via a mixture of alcohols of 13 carbon atoms). An example of a suitable cycloaliphatic amine is cyclohexylamine, whilst benzylamine is an example of a suitable araliphatic amine.

The amine to be used according to the invention may contain further substituents, eg. hydroxyl, alkoxy or alkylamino groups. Specific examples of suitable compounds are monoethanolamine and 3-dimethylamino-1-propylamine.

The reaction of the isophytol or phytol, which has been pretreated according to the invention, with trimethylhydroquinone may be carried out by conventional methods at from 60° to 200° C., especially from 80° to 140° C. and preferably from 90° to 110° C., in hydrocarbons, eg. toluene, xylene, octane, hexane, decane and especially n-heptane, as the solvent. The amount of solvent can be varied within wide limits and may be from one to ten parts by weight per part by weight of isophytol or phytol. The amount of zinc chloride can be from 0.04 part by weight, per part by weight of isophytol or phytol, up to very large amounts, of 0.5 part by weight or even more, though such large amounts offer no advantage. Proton donors which may be used are aqueous acids, eg. concentrated hydrochloric acid and concentrated hydrobromic acid, or strong mineral acids, eg. sulfuric acid or sodium bisulfate, as described in German Laid-Open Application No. 2,208,795. Amongst these proton donors, hydrochloric acid is preferred.

Toluenesulfonic acid, and mixtures of the acids mentioned, may also be used. Specifically, any strong protonic acid may be employed.

The water produced by the reaction may be removed from the system, but the conversion to d,l-α-tocopherol can also be effected without such removal of water.

Instead of using aqueous hydrochloric acid, hydrogen chloride gas, which is passed into the reaction mixture during the reaction, may equally well be employed.

It has the advantage that the acid concentration cannot rise too high, since excess hydrogen chloride gas volatilizes from the reaction mixture. In contrast, a high-boiling acid, eg. sulfuric acid, may favor the formation of by-products if it is present in too high a concentration.

The mechanism of action of the amine treatment is unknown and has hitherto defied elucidation. The treatment of the isophytol or phytol with amine particularly prevents the formation of higher-boiling impurities during the synthesis of tocopherol. However, the amount of impurities boiling slightly below tocopherol acetate is also reduced. Accordingly, the treatment of isophytol with amine results in a purer vitamin E, in higher yield.

In the Examples which follow, parts are by weight and bear the same relation to parts by volume as that of the liter to the kilogram.

EXAMPLE 1

1 part of crude isophytol of 95% purity, corresponding to 0.95 part of isophytol, is mixed with 0.002 part of methylamine whilst stirring and the mixture is heated at 90° C. for 3 hours. After cooling, the isophytol is used directly for condensing with trimethylhydroquinone.

The amine-treated isophytol is added dropwise in the course of one hour, whilst stirring, to a boiling mixture of 2.4 parts by volume of n-heptane and 0.08 part of zinc chloride and 0.49 part of trimethylhydroquinone. Hydrogen chloride gas is passed through the mixture in an amount such that the mixture remains just saturated. This is achieved by ensuring that a little hydrogen chloride escapes, partially entraining the water produced, in accordance with the vapor pressure. After cooling the reaction mixture, the latter is extracted with 10 parts of a 50% strength methanol/water mixture to remove excess trimethylhydroquinone and zinc chloride.

The heptane solution which remains is concentrated to dryness, 0.48 part of acetic anhydride is added to the residue, ie. to the crude tocopherol, the mixture is boiled for 4 hours under reflux and the unconverted acetic anhydride and the acetic acid formed are distilled off. The tocopherol acetate which remains is distilled under reduced pressure. The fraction which boils at 180°–215° C./0.001 mm Hg is d,l-α-tocopherol acetate and is separated off. 1.45 parts of vitamin E acetate of 93% purity are obtained, corresponding to a content of impurities of 7%, measured by means of gas chromatography, with an internal standard.

The yield of pure vitamin E acetate is accordingly 88.5% of theory, based on trimethylhydroquinone employed.

EXAMPLE 2

One part of crude isophytol, of 95% purity, corresponding to 0.95 part of isophytol, is mixed with 0.002 part of monomethylamine and the mixture is heated at 150° C. for one minute. The further reaction to give vitamin E is carried out as described in Example 1. 1.42 parts of vitamin E of 93.5% purity are obtained. The yield of pure vitamin E acetate is 87.2% of theory, based on trimethylhydroquinone employed.

EXAMPLE 3

One part of crude isophytol of 95% purity, corresponding to 0.95 part of isophytol, is mixed with 0.002 part of monomethylamine and this mixture is kept for 3 days at 30° C. The further reaction, to give vitamin E, is carried out as described in Example 1. 1.46 parts of vitamin E of 92% purity are obtained. The yield is 88.7% of theory.

EXAMPLE 4

One part of dehydroisophytol is mixed with 0.0029 part by weight of monomethylamine. After adding 0.02 part by weight of catalyst, containing 0.7% of palladium and 3% of zinc on calcium carbonate as a carrier, hydrogenation is carried out for from 12 to 16 hours at 60° C. and 1 atmospheric gauge hydrogen pressure. After one mole of hydrogen has been taken up per mole of dehydroisophytol, the hydrogenation is discontinued, the catalyst is filtered off and the isophytol is converted to d,l-α-tocopherol acetate as described in Example 1.

d,l-α-Tocopherol acetate, of 93.5% purity as measured by means of gas chromatography, with an internal standard, is obtained in a yield of 89% of theory.

EXAMPLES 5 TO 18

One part of crude isophytol of 95% purity, corresponding to 0.95 part of isophytol, is mixed with the amount, shown in column 3, of an amine from the Table which follows, and this mixture is kept at the temperature shown in column 5 for the period shown in column 4. The further working up to give vitamin E is carried out as described in Example 1, but the distillation of the d,l-α-tocopherol acetate is dispensed with and the content of d,l-α-tocopherol acetate is determined by gas chromatography. Crude d,l-α-tocopherol acetate is obtained in the yield shown in column 6, and in the purity shown in column 7. The yield is calculated as pure d,l-α-tocopherol acetate, based on trimethylhydroquinone employed.

TABLE

| 1 | 2 | 3 | 4 | 5 | 6 | 7 |
|---|---|---|---|---|---|---|
| Example | Amine | Amount of amine, parts per part of crude isophytol | Period of treating with amine hours | Treatment temperature °C. | Yield % of theory | Purity, % |
| 5 | Blank experiment, without amine | — | — | — | 80.6 | 80.4 |
| 6 | n-butylamine | 0.002 | 5 | 100 | 86.8 | 87.0 |
| 7 | 2-butylamine | 0.0045 | 5 | 100 | 82.4 | 83.4 |
| 8 | iso-butylamine | 0.0045 | 5 | 100 | 86.3 | 86.3 |
| 9 | n-propylamine | 0.0033 | 5 | 100 | 86.7 | 85.7 |
| 10 | iso-propylamine | 0.0033 | 5 | 100 | 84.1 | 83.3 |
| 11 | cyclohexylamine | 0.006 | 5 | 100 | 85.7 | 84.9 |
| 12 | stearylamine | 0.017 | 5 | 100 | 91.5 | 89.5 |
| 13 | benzylamine | 0.007 | 5 | 100 | 85.9 | 86.2 |

TABLE -continued

| Example | Amine | Amount of amine, parts per part of crude isophytol | Period of treating with amine hours | Treatment temperature °C. | Yield % of theory | Purity, % |
| --- | --- | --- | --- | --- | --- | --- |
| 14 | mono-2-ethylhexylamine | 0.0083 | 5 | 100 | 85.8 | 86.1 |
| 15 | monoethanolamine | 0.004 | 5 | 100 | 83.8 | 84.4 |
| 16 | diethylamine | 0.0047 | 5 | 100 | 83.0 | 82.5 |
| 17 | tridecylamine | 0.013 | 5 | 100 | 91.2 | 88.7 |

EXAMPLE 19

One part of phytol is mixed with 0.002 part of monomethylamine and this mixture is kept at 100° C. for 5 hours. The further reaction to give vitamin E is carried out as described in Example 1, but the distillation of the crude d,l-α-tocopherol acetate is dispensed with and the amount of product and its purity is determined by gas chromatography. An 80% yield of d,l-α-tocopherol acetate is obtained, the undistilled product being 81% pure, as determined by gas chromatography.

If the phytol is employed with pretreatment, a 77% yield of d,l-α-tocopherol acetate is obtained and the purity of the undistilled product is 76%.

We claim:

1. In a process for the manufacture of tocopherol by reacting 2,3,5-trimethylhydroquinone with isophytol or phytol in a hydrocarbon solvent in the presence of zinc chloride and a strong protonic acid, the improvement which comprises: carrying out the reaction with isophytol or phytol which has been treated at a temperature of from about 20° C. to 200° C. with from about 0.05 to 5 percent by weight, based on the weight of isophytol or phytol, of ammonia or a primary or secondary aliphatic, cycloaliphatic or araliphatic amine having 1 to 20 carbon atoms in the chain.

2. A process as claimed in claim 1, wherein the reaction is carried out with isophytol or phytol which has been treated with an amine.

3. A process as claimed in claim 2 wherein the isophytol or phytol has been treated with a low molecular weight aliphatic primary monoamine.

4. A process as claimed in claim 2, wherein the amine is monomethylamine.

5. A process as claimed in claim 2, wherein the amine is stearylamine.

6. A process as claimed in claim 2, wherein the amine is tridecylamine.

7. A process as claimed in claim 1, wherein the reaction is carried out with isophytol which has been manufactured by catalytic hydrogenation of dehydroisophytol in the presence of an amine.

8. A process as set forth in claim 1, wherein the strong acid is hydrochloric acid.

9. A process as set forth in claim 1, wherein the acid is hydrogen chloride gas.

10. A process as set forth in claim 9, wherein the amount of hydrogen chloride gas present during the reaction is sufficient to saturate the reaction solution.

11. A process as set forth in claim 1, wherein the strong acid is sodium bisulfate.

12. A process as set forth in claim 2, wherein the isophytol or phytol has been treated with from 0.1 to 2 percent by weight of an amine, based on the weight of isophytol or phytol.

13. A process as set forth in claim 12, wherein the treatment is carried out at a temperature of from 50°–100° C.

* * * * *